United States Patent
Odagiri et al.

(10) Patent No.: US 11,053,469 B2
(45) Date of Patent: *Jul. 6, 2021

(54) CULTURE BAG, AND CULTURE APPARATUS

(71) Applicant: Dexerials Corporation, Tokyo (JP)

(72) Inventors: Hirokazu Odagiri, Sendai (JP);
Yasuyuki Kudo, Shimotsuke (JP);
Rishabh Gupta, Shimotsuke (JP); Keiji Honjo, Kiyose (JP)

(73) Assignee: Dexerials Corporation, Tokyo (JP)

( * ) Notice: Subject to any disclaimer, the term of this patent is extended or adjusted under 35 U.S.C. 154(b) by 204 days.

This patent is subject to a terminal disclaimer.

(21) Appl. No.: 15/982,120

(22) Filed: May 17, 2018

(65) Prior Publication Data

US 2018/0340140 A1 Nov. 29, 2018

(30) Foreign Application Priority Data

May 24, 2017 (JP) .............................. JP2017-103123

(51) Int. Cl.
*C12M 3/00* (2006.01)
*C12M 1/00* (2006.01)
*C12M 1/04* (2006.01)
*C12M 1/34* (2006.01)
*C12M 3/06* (2006.01)

(52) U.S. Cl.
CPC ............ *C12M 23/14* (2013.01); *C12M 23/02* (2013.01); *C12M 23/24* (2013.01); *C12M 23/26* (2013.01); *C12M 27/16* (2013.01); *C12M 41/34* (2013.01)

(58) Field of Classification Search
CPC .............................. C12M 25/14; C12M 23/14
See application file for complete search history.

(56) References Cited

U.S. PATENT DOCUMENTS 5,151,366 A * 9/1992 Serkes ................... C12M 23/08
422/547
5,272,084 A * 12/1993 O'Connell ............. C12M 23/08
215/DIG. 3

(Continued)

FOREIGN PATENT DOCUMENTS

JP 2010540228 A 12/2010
JP 2014239675 A 12/2014

OTHER PUBLICATIONS

Feb. 2, 2021, Notification of Reasons for Refusal issued by the Japan Patent Office in the corresponding Japanese Patent Application No. 2017-103123.

(Continued)

*Primary Examiner* — Nathan A Bowers
(74) *Attorney, Agent, or Firm* — Kenja IP Law PC (57) ABSTRACT

Provided is a culture bag accommodating a culture fluid, the culture bag is capable of suppressing foaming in the culture fluid when oscillating the culture fluid to perform a culture, and performing a culture with high efficiency. The culture bag includes a culture space accommodating a culture fluid, the culture space being an endless space to allow the culture fluid to circulate therein, in which the culture bag has an inner surface that comes into contact with the culture fluid to be accommodated therein, the inner surface including, at least in part thereof, a concave-convex region having a concave-convex structure.

4 Claims, 8 Drawing Sheets

(56) References Cited

U.S. PATENT DOCUMENTS

| | | | | |
|---|---|---|---|---|
| 2004/0191895 A1* | 9/2004 | Whitley | ................ | C12M 23/08 |
| | | | | 435/299.2 |
| 2008/0274541 A1* | 11/2008 | Selker | ................ | B01F 3/04248 |
| | | | | 435/289.1 |
| 2009/0170190 A1* | 7/2009 | Nishi | .................... | C12M 23/12 |
| | | | | 435/299.1 |
| 2011/0014689 A1* | 1/2011 | Gandlur | ............. | B01F 11/0028 |
| | | | | 435/289.1 |

OTHER PUBLICATIONS

Apr. 13, 2021, Decision of Refusal issued by the Japan Patent Office in the corresponding Japanese Patent Application No. 2017-103123.

* cited by examiner

CULTURE BAG, AND CULTURE APPARATUS

TECHNICAL FIELD

The present disclosure relates to a culture bag and a culture apparatus.

BACKGROUND

Disposable culture bags have conventionally been used for culturing microorganisms and animal and plant cells. Culture bags are typically formed of a bag body made of a flexible resin, and accommodate therein a culture fluid suspending culture targets such as cells at a given concentration (number).

When performing a culture in such culture bags, in general, culture fluids need to be favorably agitated; high agitation performance of the culture fluid allows circulation of nutrients, and maintains gas components such as oxygen and carbon dioxide being dissolved in the culture fluid, which promotes growth of culture targets, to thereby improve culture efficiency.

Various studies have been conducted to address such demand. For example, Patent Literature 1 discloses, as a technology applicable to cell culture, a mixing container provided with baffles, in which the container is oscillated along a movable axis, to thereby cause a vortex motion in the liquid in the container so as to effect efficient mixture.

CITATION LIST

Patent Literature

PTL 1: JP2010-540228A

SUMMARY

However, when the aforementioned agitation through oscillation of the mixing container is directly applied to cell culture, the culture fluid collides with the baffles in the container to create waves, and the waves catch gas therein which generates babbles and foams when the waves falling on the fluid surface. Then, the babbles and foams rupture in the culture fluid to induce an impact, which causes damage to the culture targets such as cells, affecting the culture. Accordingly, the aforementioned technology still needs to be improved in terms of suppressing the occurrence of foaming while obtaining high agitation performance as well as high culture efficiency.

It could therefore be helpful to provide a culture bag capable of suppressing the occurrence of foaming when oscillating the culture fluid to perform a culture, and performing a culture with high efficiency, and a culture apparatus including the culture bag.

The present disclosure therefore provides the followings:

<1> A culture bag including a culture space accommodating a culture fluid, in which:

the culture space is an endless space that allows the culture fluid to circulate therein; and the culture bag has an inner surface that comes into contact with the culture fluid to be accommodated therein, the inner surface including, at least in part thereof, as a concave-convex region having a concave-convex structure.

<2> The culture bag according to the foregoing <1>, in which the concave-convex region has a composite structure including the concave-convex structure and a fine structure formed on a surface of the concave-convex structure.

<3> The culture bag according to the foregoing <1> or <2>, in which the fine structure has a fine concave-convex pattern with a height h of 200 nm or more and less than 1 mm, a width w of 200 nm or more and less than 1 mm, and a pitch p of 200 nm or more and less than 1 mm.

<4> The culture bag according to the foregoing <3>, having an aspect ratio h/w of 0.5 or more.

<5> The culture bag according to any of the foregoing <1> to <4>, in which the concave-convex structure has a concave-convex pattern with a height H of 10 mm or less, a width W of 100 mm or less, and a pitch P of 100 mm or less.

<6> The culture bag according to the foregoing <5>, having an aspect ratio H/W of 0.1 or more.

<7> The culture bag according to any of the foregoing <1> to <6>, in which the culture space is a doughnut-like space.

<8> A culture apparatus comprising the culture bag according to any of the foregoing <1> to <7>.

The present disclosure therefore provides: a culture bag accommodating a culture fluid to be agitated to perform a culture, the culture bag being capable of suppressing the occurrence of foaming, to thereby perform a culture with high efficiency; and a culture apparatus including the culture bag.

DETAILED DESCRIPTION

Hereinafter, the present disclosure is described in detail with reference to embodiments.

(Culture Bag)

The disclosed culture bag according to an embodiment (which may also be referred to as "culture bag of this embodiment" in below) includes a culture space for accommodating a culture fluid, the culture space being an endless space that allows the culture fluid to circulate therein, in which the culture bag has an inner surface that comes into contact with the culture fluid to be accommodated therein, the inner surface including, at least in part thereof, a concave-convex region having a concave-convex structure. Here, the culture bag of this embodiment may also include: a port for supplying a mixed gas of oxygen and carbon dioxide with controlled concentration; a port for supplying or recovering the culture fluid; and a port for acquiring a sample.

As understood from the above, the culture bag of this embodiment includes an endless culture space that allows the culture fluid to circulate therein, and also includes a concave-convex region formed at least in part of the inner surface that comes into contact with the culture fluid to be accommodated therein. Accordingly, when the culture bag accommodating the culture fluid therein is oscillated, the culture fluid circulates as passing over the concave-convex region, without generating a region where the velocity of flow of the culture fluid becomes substantially zero (which is so-called stagnation) while resultantly causing the culture fluid to flow in various directions (vectors) at various rates, which increases the agitating performance and even allows for highly efficient culture. Further, the culture bag of this embodiment allows the culture fluid to circulate in an endless space, which suppresses the collision between the inner surface of the culture space and the culture fluid, generating smaller waves of the culture fluid. As a result, the culture bag of this embodiment can significantly suppress the occurrence of foaming, as compared with the case where baffles or the like are provided to agitate the culture fluid.

Note that even a culture bag including a culture space that is not "endless to allow the culture fluid to circulate therein", for example, such culture bag can be considered to still generate, to a certain degree, the flows of the culture fluid in various directions (vectors) at various rates, as long as at least part of the inner surface that comes into contact with the culture fluid to be accommodated therein has a concave-convex region, and to suppress the occurrence of foaming as compared with a culture bag having baffles or the like.

<Culture Space>

Figure 1:
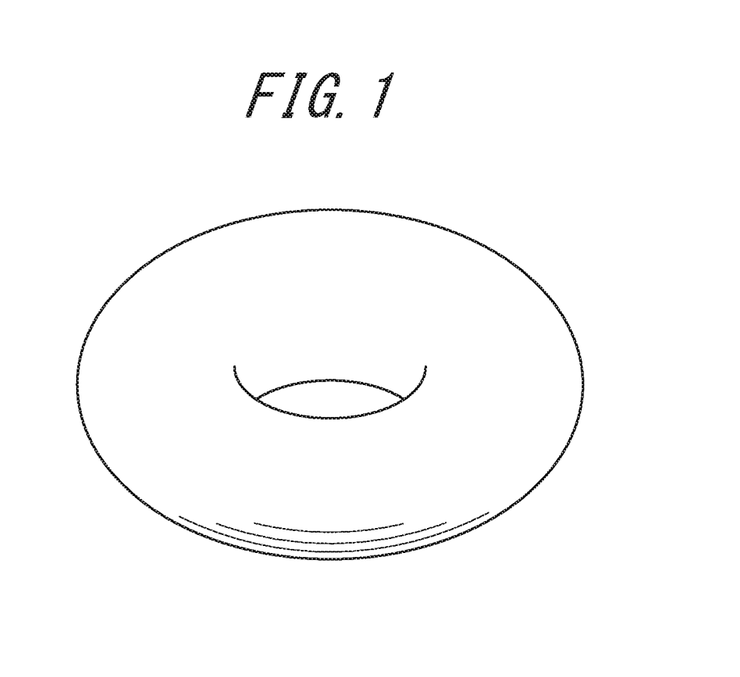
FIG. 1 is a schematic diagram illustrating an exemplary shape of the disclosed culture bag according to an embodiment.

The culture bag of the embodiment includes a culture space to accommodate a culture fluid, and the culture space is an endless space that allows the culture fluid to circulate. In particular, the culture space may preferably be a doughnut-like space as illustrated in FIG. 1. The culture space being formed as a doughnut-like space can further suppress collision between the circulating culture fluid and the inner surface, and also suppress generation of waves and occurrence of foaming in the culture fluid.

Here, the term "doughnut-like" as used herein in relation to the culture space is not limited to those being a true circle in section of the culture space taken along a line perpendicular to the circulating direction of the culture fluid, and should also include those being, for example, an oval shape or any shape defined by arbitrary arcs and line segments. Further, the term "doughnut-like" as used herein in relation to the culture space is not limited to those being a true circle in shape formed by a main circulation path of the culture fluid, and may include those being, for example, an oval shape or any shape defined by arbitrary arcs and line segments.

<Inner Surface>

In the culture bag of this embodiment, the inner surface that comes into contact with the culture fluid to be accommodated therein has, at least in part thereof, a concave-convex region having a concave-convex structure. Here, whether or not an arbitrary inner surface of the culture bag corresponds to the "inner surface that comes into contact with the culture fluid to be accommodated therein" may vary depending on the amount of the culture fluid to be accommodated therein. In consideration thereof, the culture bag of this embodiment may preferably have the aforementioned concave-convex region having the concave-convex structure in the inner surface at the bottom.

Further, in the culture bag of this embodiment, the structure of the inner surface not in contact with the culture fluid accommodated therein is not particularly limited.

Figure 2:
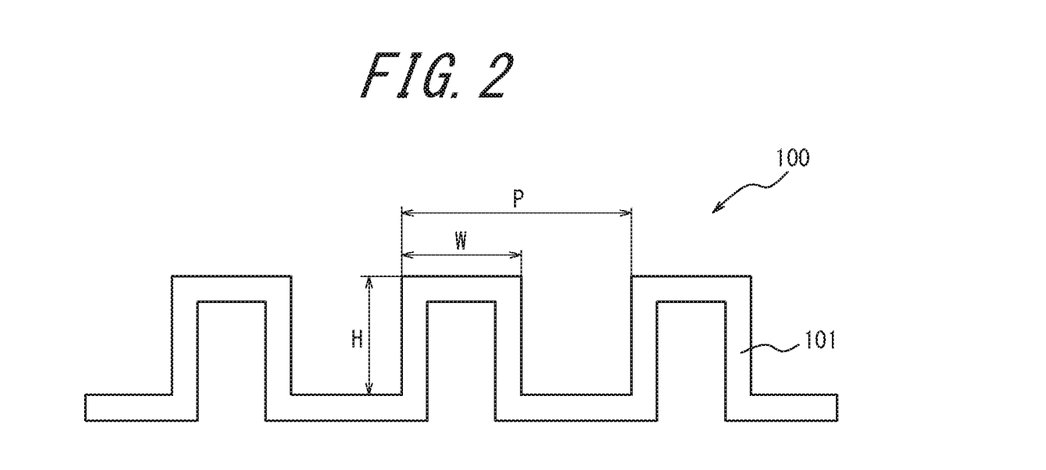
FIG. 2 is a schematic section of a structural example of a concave-convex region in an inner surface of the disclosed culture bag according to an embodiment.
Figure 3:
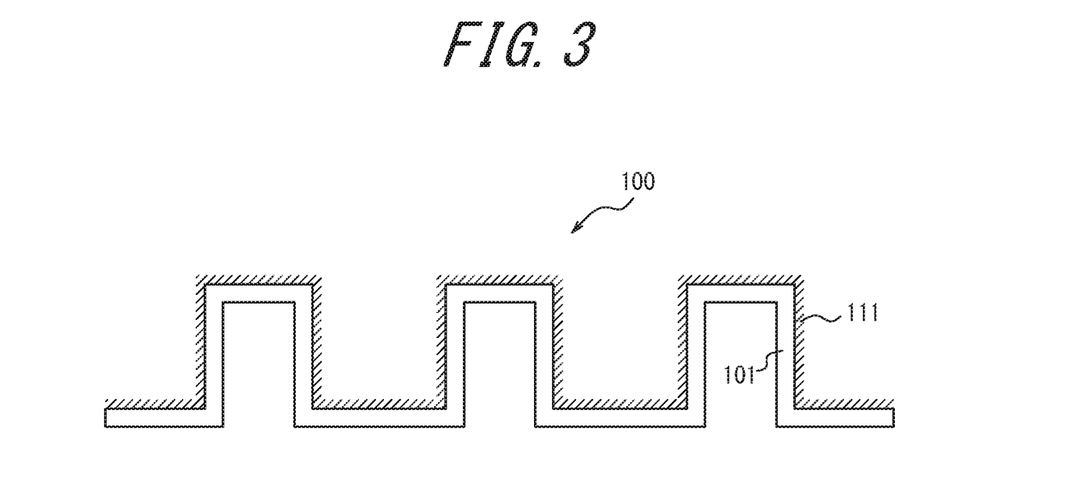
FIG. 3 is a schematic section of a structural example of a concave-convex region in an inner surface of the disclosed culture bag according to an embodiment.

The concave-convex structure is not particularly limited, and may be an arbitrary concave-convex structure having a regular concave-convex pattern or an irregular concave-convex pattern. For example, as illustrated in FIG. 2, the concave-convex structure 101 may preferably have a concave-convex pattern with a height (H) of 10 mm or less, a width (W) of 100 mm or less, and a pitch (P) of 100 mm or less.

Further, the concave-convex structure having the aforementioned concave-convex pattern may preferably have an aspect ratio H/W of 0.1 or more. The aspect ratio of 0.1 or more can more reliably generate the flow of the culture fluid having various velocity distributions. From the same point of view, the aspect ratio H/W may preferably be 0.2 or more, and further preferably be 0.3 or more. The aspect ratio H/W may preferably be 2 or less, without being particularly limited.

Further, the concave-convex region of the inner surface that comes into contact with the culture fluid to be accommodated therein may preferably have a composite structure formed of the aforementioned concave-convex structure 101 and the fine structure 11 formed on the surface of the concave-convex structure 101. In this regard, a liquid (Newtonian fluid) passing over a fine structure body leads to a significant change in velocity at the interface between the liquid and the fine structure. Accordingly, the aforementioned composite structure including a fine structure further increases the variety of the flows of the culture fluid when oscillated, to thereby further increase sufficiently the culture efficiency.

Here, the "fine structure" disclosed herein refers to a structure having irregularities on the order of μm and/or on the order of nm, without including irregularities on the order of mm.

Figure 4:
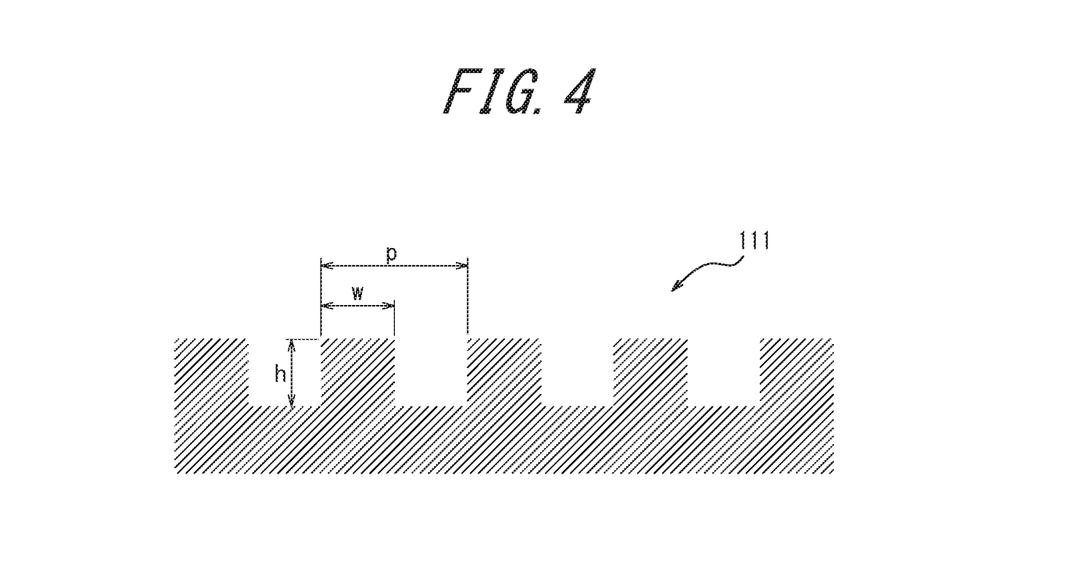
FIG. 4 is a schematic diagram of a structural example of a fine structure in an inner surface of the disclosed culture bag according to an embodiment.

The fine structure may be any fine structure without being particularly limited, and may preferably be a structure having a regular pattern. Specifically, as illustrated in FIG. 4, the fine structure 111 may preferably have a fine concave-convex pattern with a height (h) of 200 nm or more and less than 1 mm, a width (w) of 200 nm or more and less than 1 mm, and a pitch (p) of 200 nm or more and less than 1 mm. This configuration allows for efficiently taking gas present in the culture space into the concave portions, to thereby efficiently provide a desired gas component (for example, oxygen) to the culture targets. Further, when the fine structure has the aforementioned fine concave-convex pattern, the height (h) thereof may preferably be 5 μm or more and 50 μm or less, the width (w) thereof may preferably be 5 μm or more and 40 μm or less, and the pitch (p) thereof may preferably be 10 μm or more and 80 μm or less, from the same point of view as above.

Further, the fine structure having a fine concave-convex pattern may be a structure having the aforementioned fine concave-convex patterns in an arbitrary one direction (so-called striped fine concave-convex structure) or may be a structure having the aforementioned fine concave-convex patterns in arbitrary two directions substantially orthogonal to each other (so-called grid fine concave-convex structure), with the grid fine concave-convex structure being preferred. The fine structure being a grid fine concave-convex structure allows for more efficiently taking gas present in the culture space into the concave portions during oscillation culture, to thereby more efficiently provide desired gas components (for example, oxygen) to the culture targets.

Here, when the fine structure employs a grid fine concave-convex structure, the height, the width, and the pitch of one fine concave-convex pattern in one direction may all be the same as or may be different from at least one of the height, the width, and the pitch in the other fine concave-convex pattern in the other direction.

Further, when the fine structure has the aforementioned fine concave-convex pattern, the aspect ratio h/w may preferably be 0.5 or more. The aspect ratio being 0.5 or more allows for efficiently taking gas present in the culture space into the concave portions during oscillation culture, to thereby more efficiently provide desired gas components (for example, oxygen) to the culture targets. From the same point of view, the aspect ratio h/w may preferably be 0.7 or more, and further preferably be 0.9 or more. Further, the aspect ratio h/w may preferably be 10 or less, without being particularly limited.

<Aspects of Concave-Convex Structure>

Figure 5A:
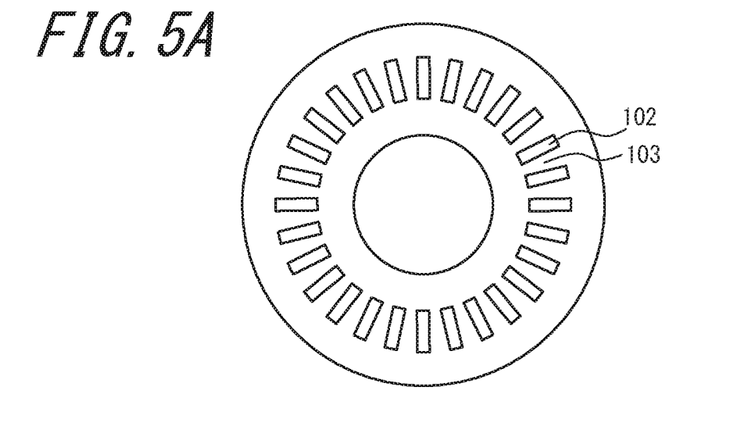
FIGS. 5A to 5C each are a schematic diagram of an exemplary concave-convex region in an inner surface of the disclosed culture bag according to an embodiment.
Figure 5B:
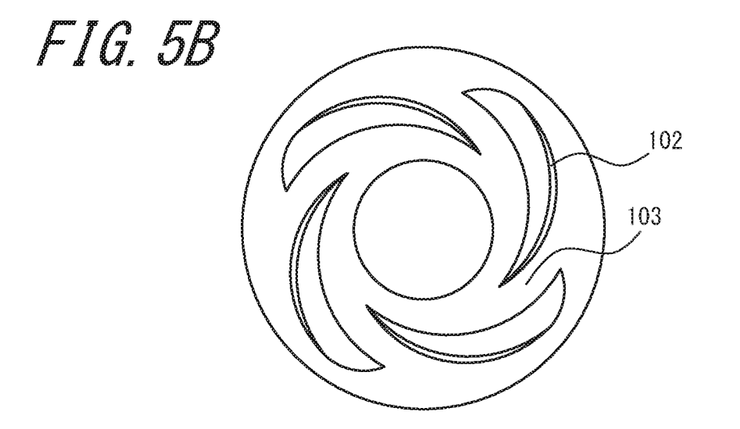
Figure 5C:
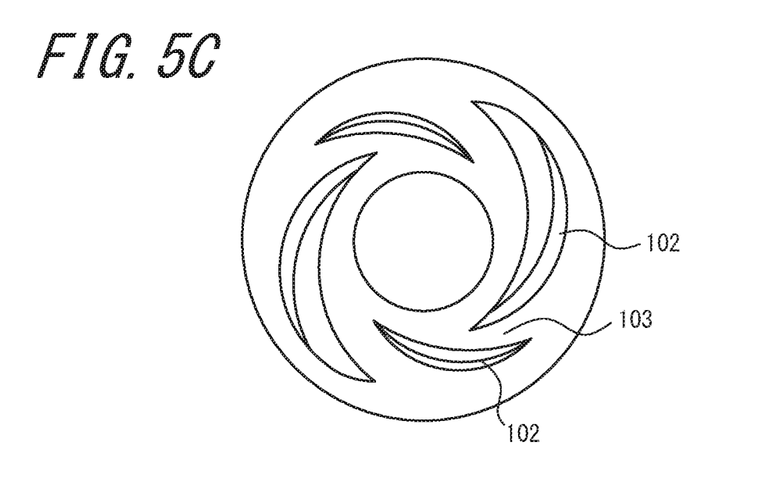

Aspects of the concave-convex structure in the culture bag of this embodiment are not particularly limited, and may be formed of a plurality of convex portions 102, each being rectangular in plan view and radially disposed at regular intervals, forming a concave-convex structure as illustrated in, for example, FIG. 5A. Further, as illustrated in FIG. 5B, for example, a plurality of convex portions 102 each being in an arbitrary shape (in a crescent shape in FIG. 5B) may be spirally disposed to form the concave-convex structure. Further, as an application of FIG. 5B, the convex portions 102 may be different from one another in size and shape (FIG. 5C).

<Manufacture of Culture Bag>

The method of manufacturing the culture bag of this embodiment is not particularly limited. The culture bag of this embodiment may be manufactured by: preparing two sheet-like bag base materials; molding each of the bag base materials with a mold so as to eventually obtain a desired three-dimensional culture space; and integrating the two bag materials thus molded facing to each other. The aforementioned exemplary method of manufacturing a culture bag is explained in below.

—Bag Base Material—

Biocompatible materials (materials non-toxic to culture targets such as cells) are preferred as the bag base material, which may include, for example: polyolefin resins such as polypropylene and polyethylene; vinyl resins such as polyvinyl acetate, polyvinyl alcohol, polyvinyl chloride, ethylene vinylalcohol copolymer resin, and ethylene vinylacetate copolymer resin; cycloolefin resins such as cycloolefin polymer (COP) and cycloolefin copolymer (COC); thermoplastic resins such as polystyrene; polyethylene terephthalate; polyurethane; polyamide; polymethyl methacrylate; and polycarbonate; ultra-violet curable resin such as acrylic resin; and an arbitrary electron-beam curable resin.

Further, the sheet-like bag base material may be formed of the aforementioned resin sheet with a nylon sheet laminated thereon. Alternatively, the sheet-like bag base material may be a laminate body having three or more layers with a sheet made of ethylene vinylalcohol copolymer (EVOH) layered in the middle.

—Molding of Bag Base Material—

Exemplary methods of molding the sheet-like bag base material may include, without being particularly limited, injection molding, blow molding, and compression molding, with compression molding being particularly preferred as the bag base material in terms of allowing the bag material to be molded with a uniform force and of eliminating the need for preparing a plurality of molds (a male mold and a female mold).

The mold to be used for the molding may be worked in advance into a structure inverted from a shape capable of eventually obtaining a desired three-dimensional culture space and from a structure (such as concave-convex structure and an arbitrary fine structure) to be formed on the inner surface of the culture bag to be eventually obtained. In the case of imparting a fine structure to the mold, a single crystal diamond bite may exemplary be used.

In molding, the bag material and/or mold may be heated in order to increase moldability. The bag material may be heated by, for example, a near infrared or far infrared halogen heater. Meanwhile, the mold may be heated by, for example, a cartridge heater embedded within the mold.

—Integration—

Then, the two molded bag base materials taken off from the mold are integrated as being brought to face each other so as to define a desired three-dimensional culture space therebetween. The molds may each have non-molding parts which serve as contact surfaces, and the surfaces may be thermally fusion-bonded (heat sealed) or bonded with an arbitrary adhesive, for example, to thereby integrate the molds. This way allows the culture bag to be manufactured.

Rather than using two bag base materials to manufacture a culture bag, a single bag base material may be properly molded and folded, for example, so as to be integrally formed.

Figure 6:
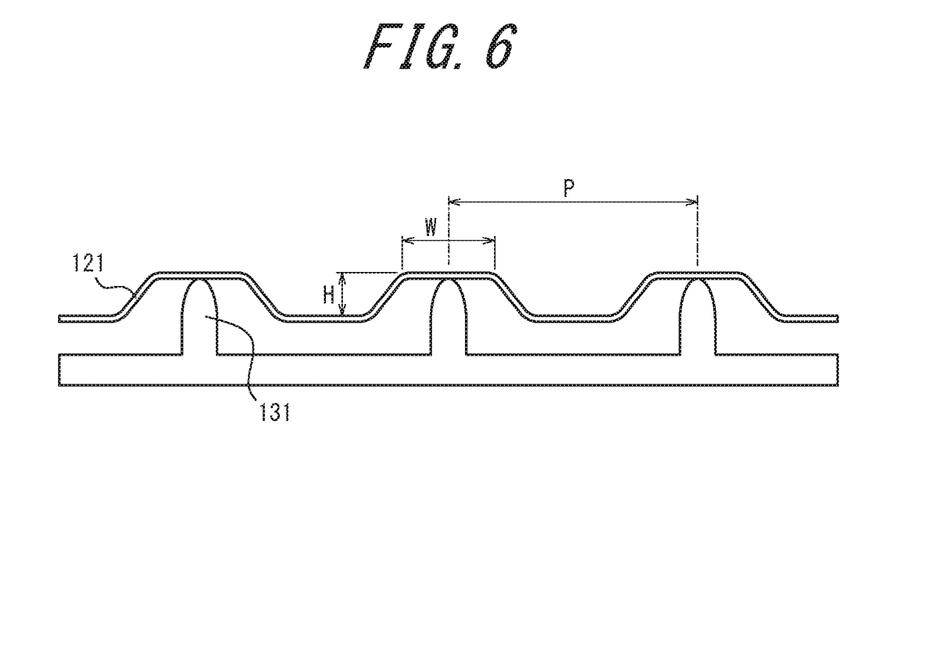
FIG. 6 is a schematic overview diagram for illustrating an exemplary method of imparting the concave-convex structure to a culture bag.

In the aforementioned method of manufacturing a culture bag, molds are used to impart a concave-convex structure in an inner surface of the culture bag. Alternatively, however, the bag base material 121 may be formed of a flexible material and a technology of externally pressing a plurality of protrusions 131 against the bag base material 121 as illustrated, for example, in FIG. 6 may be employed, so as to impart a concave-convex structure in the inner surface of the culture bag.

(Culture Apparatus)

The disclosed culture apparatus according to an embodiment (which may also be referred to as "culture apparatus of this embodiment" in below) is provided with the aforementioned culture bag. The culture apparatus of this embodiment, which includes the aforementioned culture bag, is capable of suppressing the occurrence of foaming while performing a culture with high efficiency. In performing a culture with the culture apparatus of this embodiment, the types of the culture targets (e.g., cells), the configuration and arrangement of the first surface and the second surface provided to the inner surface of the culture bag, and the oscillation conditions may properly be combined.

Further, the culture apparatus of this embodiment may further include, for example, a culture fluid supply mechanism, a culture fluid recovery mechanism, an oscillating mechanism, and a timer mechanism, as long as being the apparatus being provided with the aforementioned culture bag.

EXAMPLES

Next, the present disclosure is more specifically described with reference to Example and Comparative Example. However, the present disclosure is not limited to Examples in below.

The culture bags fabricated in Example and Comparative Example were evaluated for the occurrence of foaming, culture efficiency, and dissolved oxygen content, according to the following procedure.

(Evaluation of Occurrence of Foaming)

A fabricated culture bag accommodating a 500 mL culture fluid was horizontally installed. The culture fluid accommodated in the culture bag was defined to have: a density of 1007.5 kg/m$^3$; a viscosity of 1.7757e$^{-6}$ m$^2$/s; and a surface tension of 0.0602 N/m. Then, the culture bag was horizontally turned (oscillated) with a turning radius of 50 mm and a turning speed (number of rotations) of 20 rpm, so as to visually observe the occurrence of foaming in the culture fluid at that time.

(Evaluation of Culture Efficiency)

The velocity distribution of the culture fluid that flows when the culture bag is oscillated as described above was obtained through simulation. Specifically, a graph of velocity distribution was created in which: the abscissa shows the average velocity of the flowing culture fluid per one cycle for each unit of account; and the ordinate represents a rate (corresponding to the probability of occurrence) of the flowing culture fluid with the entire unit of account being defined as 1. In the aforementioned graph, the broader the peak shape, the more the amount of flow varies, which means that the agitation performance is favorable, leading to high culture efficiency.

(Evaluation of Dissolved Oxygen)

The distribution of dissolved oxygen concentrations of the culture fluid that flows when the culture bag is oscillated as described above was obtained through simulation. This simulation was targeted for a partial region (6 mm×1 mm) on the inner surface of the culture bag, with the amount of oxygen contained in the culture fluid contained being 0 in the initial state. Then, the dissolved oxygen concentrations in the culture fluid having passed through the aforementioned region were illustrated in a shaded view. The lighter (whiter) color represents higher concentration of dissolved oxygen in the culture fluid having passed through the aforementioned region. Further measured was an average value of the dissolved oxygen concentrations in the culture fluid having passed through the aforementioned region.

Example 1

<Preparation of Mold>

An aluminum alloy sheet (A7075) was prepared as the mold material. This alloy sheet was processed into a shape having a contour of the upper half of a doughnut-like shape, to thereby fabricate a mold A. Separately from the mold A, the aforementioned alloy sheet was processed into a shape having a contour of the upper half of a doughnut-like shape, in which a concave-convex structure on the order of mm was formed in the uppermost part of the doughnut-like shape by an ultra precision machine and then the surface of the concave-convex structure was processed into a fine concave-convex structure using a single crystal diamond bite, to thereby fabricate a mold B. Here, the concave-convex structure and the fine concave-convex structure mentioned above are configured to have a structure inverted from a structure to be formed in the inner surface of the culture bag to be eventually obtained.

<Fabrication of Culture Bag>

The culture bag was fabricated by compression molding using the aforementioned molds.

Specifically, first, as the material for the bag base material, a 0.3 mm-thick sheet of linear low density polyethylene (LLDPE) (which may also be simply referred to as "resin sheet" in below) was prepared. The aforementioned resin sheet was installed in a chamber so as to partition the chamber into an upper chamber and a lower chamber, with the mold A being installed in the lower chamber. Next, the upper chamber and the lower chamber were each made into a vacuum state, and heated the resin sheet to 150° C. and the mold A to 230° C., respectively. Then, pressure in the upper chamber was returned to the atmospheric pressure, and the resin sheet softened due to the heating was arranged along the mold A. After that, compressed air of 0.31 MPa was supplied from the upper chamber side so as to press the resin sheet to the mold A. Thereafter, with the supply of compressed air being continued, the resin sheet was cooled to 50° to be solidified, and pressures in the upper and lower chambers are each returned to the atmospheric pressure. Then, the sheet was taken off from the mold A to thereby obtain a bag material A. Further, a bag material B was similarly obtained in the same manner as above except using the mold B in place of the mold A.

Then, the bag material A and the bag material B were brought to face each other so as to define a doughnut-like space therebetween, and the contact surfaces were heat sealed to integrate the both, to thereby fabricate a culture bag.

Figure 7:
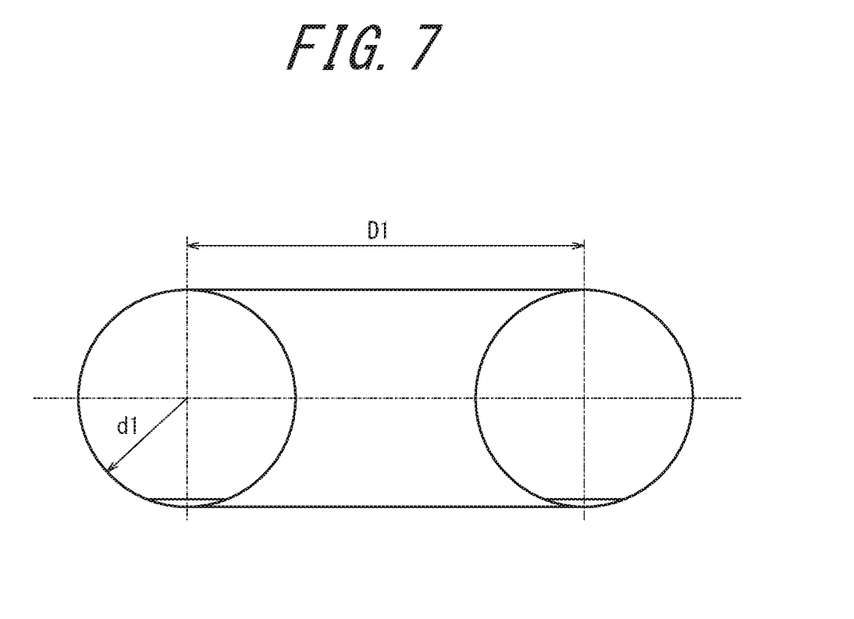
FIG. 7 is a schematic section of the disclosed culture bag according to Example.
Figure 8:
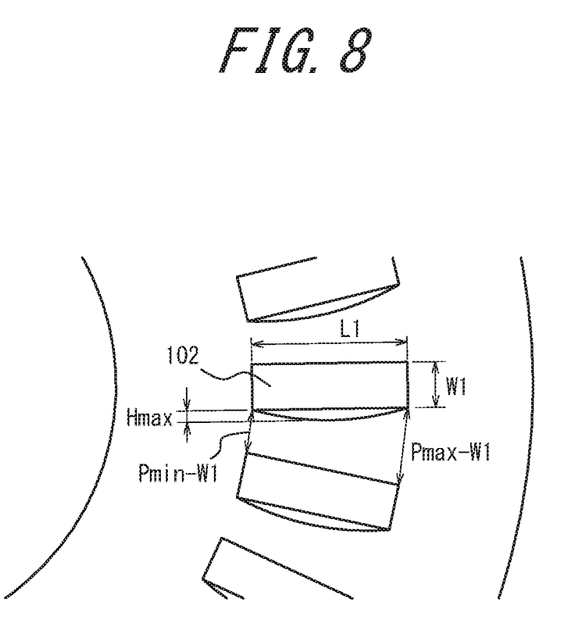
FIG. 8 is a partially-enlarged schematic section of the inner surface of the disclosed culture bag according to Example.
Figure 9:
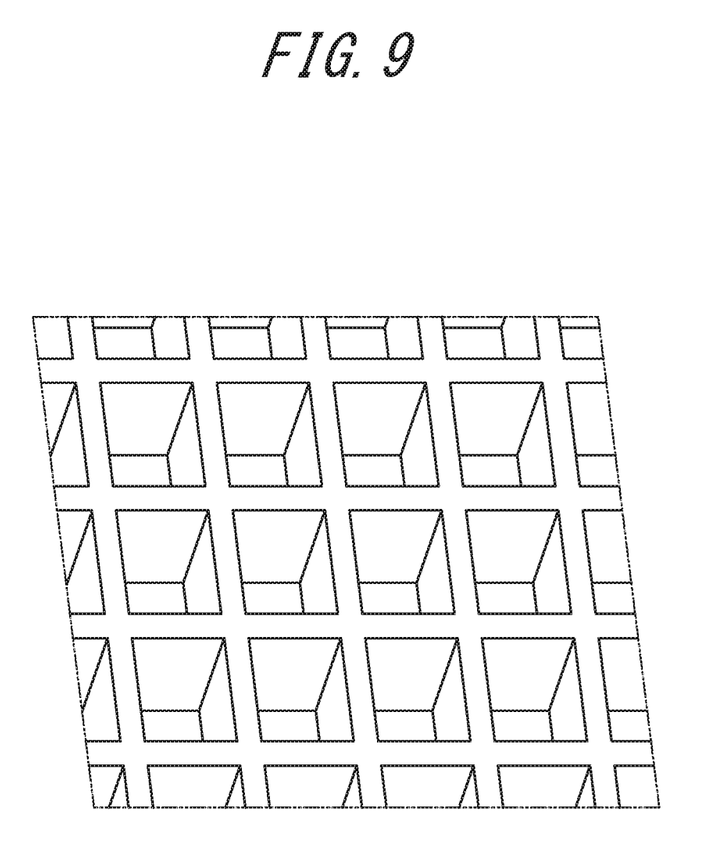
FIG. 9 is a schematic diagram illustrating a grid fine concave-convex structure in an inner surface of the disclosed culture bag according to Example.

As illustrated in FIG. 7, the culture bag fabricated in Example 1 had a doughnut-like culture space with a center diameter D1 of 180 mm, and the flow path of the culture fluid had a circular cross section with a radius d1 of 30 mm. Further, the bag base material B at the bottom side in use had a plurality of convex portions, each being rectangular in plan view, radially disposed at equal intervals, to thereby form a concave-convex structure in the inner surface as illustrated in FIG. 5A. Referring to FIG. 8, the convex portions in the concave-convex structure each had a width (W1) of 10 mm, a length (L1) of 25 mm, and a maximum height (H$_{max}$) of 3 mm, with the minimum interval (approximated by P$_{min}$−W1) between the adjacent convex portions being 18 mm and the maximum interval (approximated by P$_{max}$−W1) being 24 mm. Further, a fine structure was formed on the surface of the concave-convex structure, and the fine structure formed a grid fine concave-convex structure having concave-convex patterns with a height (h) of 30 μm, a width (w) of 33.6 μm, and a pitch (p) of 63.6 μm in two directions orthogonal to each other. For reference, FIG. 9 illustrates a schematic diagram of a grid fine concave-convex structure.

Then, the occurrence of foaming in the culture bag fabricated in Example 1 was visually observed according to the aforementioned procedure. As a result, the occurrence of foaming was hardly observed. Significant reduction of foaming was confirmed in Example 1, as compared with a conventional culture bag provided with baffles.

Figure 10:
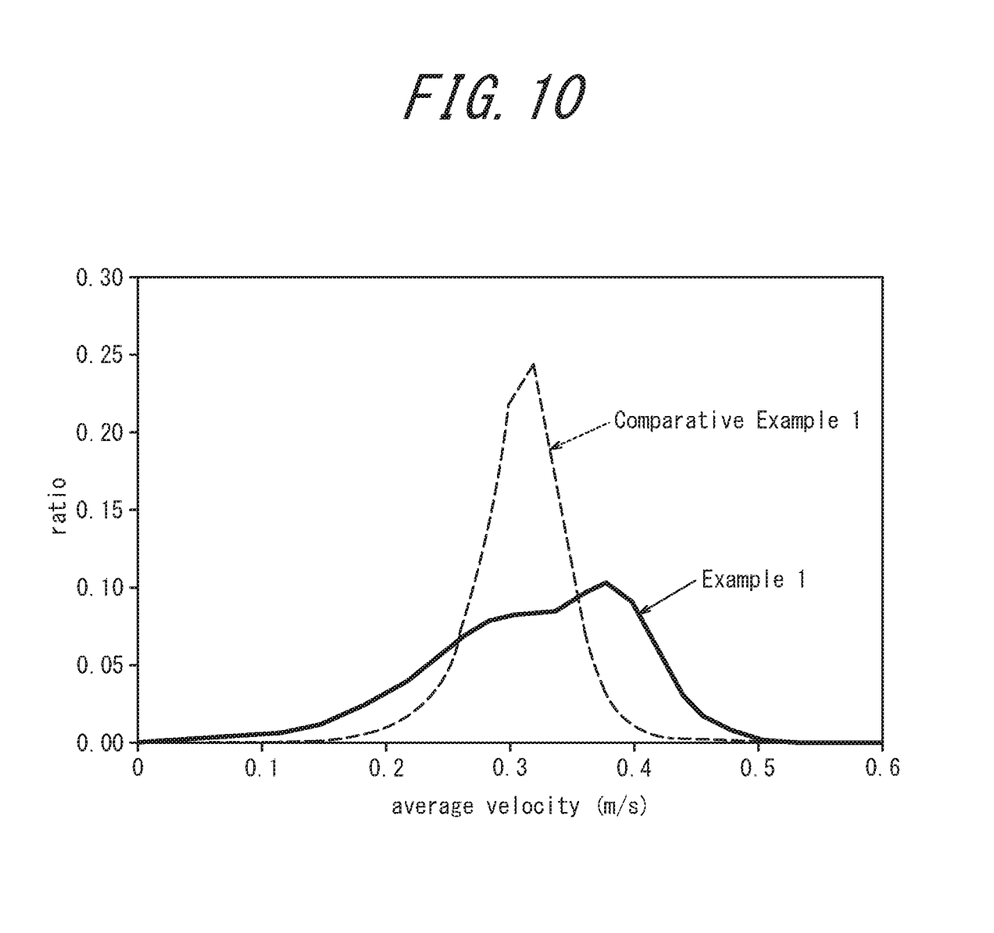
FIG. 10 is a graph illustrating velocity distributions of culture fluids that flow in the culture bags of Example and of Comparative Example when oscillated.
Figure 11A:
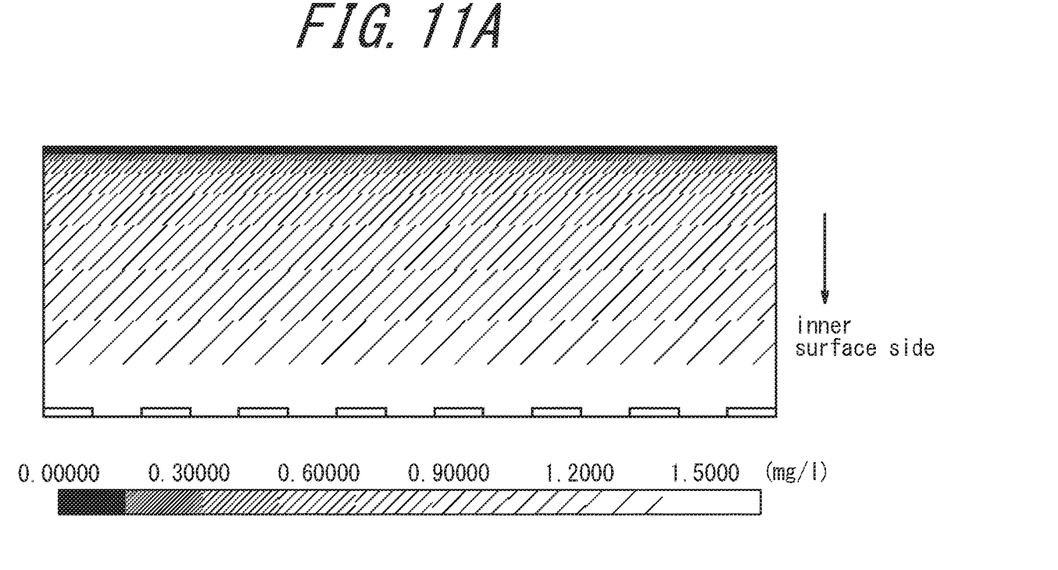
FIGS. 11A and 11B are distribution charts of dissolved oxygen concentrations in the culture bags of Example and Comparative Example.

Further, for evaluating the culture efficiency, FIG. 10 illustrates a graph of velocity distribution in Example 1 created according to the aforementioned procedure. Further, for evaluating dissolved oxygen content, FIG. 11A is a distribution chart of dissolved oxygen concentrations in Example 1 created according to the aforementioned procedure, and Table 1 shows the measurement result of average values of the dissolved oxygen concentrations.

Comparative Example 1

The mold A was used in place of the mold B. Then, similarly to Example 1, two bag base materials A were obtained to thereby fabricate a culture bag.

Here, the culture bag fabricated in Comparative Example 1 had a doughnut-like culture space with a center radius D1 of 180 mm and the flow path of the culture fluid had a circular cross section with a radius d1 of 30 mm. However, the bag base material A fabricated in Comparative Example 1 neither had a concave-convex structure nor a fine structure in the inner surface thereof.

The occurrence of foaming in the culture bag fabricated in Comparative Example 1 was visually observed according to the aforementioned procedure. As a result, the occurrence of foaming was hardly identified.

Figure 11B:
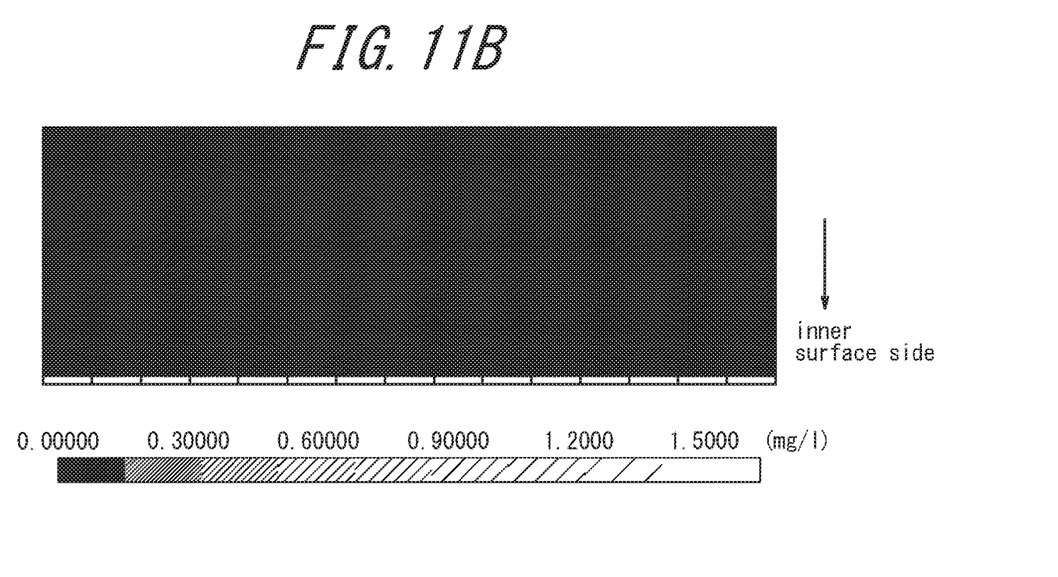

Further, for evaluating the culture efficiency, FIG. 10 illustrates a graph of velocity distribution in Comparative Example 1 created according to the aforementioned procedure. Further, for evaluating dissolved oxygen content, FIG. 11B is a distribution chart of dissolved oxygen concentrations in Comparative Example 1 created according to the aforementioned procedure, and Table 1 shows the measurement result of average values of the dissolved oxygen concentrations.

TABLE 1

|  | Average Value of Dissolve Oxygen Concentration (mg/L) |
|---|---|
| Example 1 | 0.219 |
| Comparative Example 1 | 0.062 |

As can be understood from FIG. 10, a large fraction of the average velocities of Comparative Example 1 was found in the vicinity of 0.3 m/s with the magnitudes of flow being uniformly distributed as a whole, whereas in Example 1, the average velocities were distributed in a range of 0.1 to 0.5 m/s, with the magnitudes of flow being nonuniform. That is, the culture bag of Example 1, which includes a concave-convex structure at least in part of the inner surface thereof, can be found to improve, when accommodating a culture fluid therein and oscillating the same for performing a culture, agitation performance while performing a culture with high efficiency.

Further, referring to FIGS. 11A and 11B, the dissolved oxygen concentration is higher as closer to the inner surface in Example 1, while no such tendency can be observed in Comparative Example 1 and the dissolved oxygen concentration was still low even in the vicinity of the inner surface. Further, referring to Table 1, it can be found that that in Example 1, the amount of oxygen dissolved in the culture fluid was three times or more higher than that of Comparative Example 1. These results may conceivably be derived from, for example, the fine concave-convex patterns provided to the culture bag of Example 1, which takes in oxygen in the concave portions while allowing the culture fluid passing near the inner surface to come into contact with the oxygen, so as to have more oxygen dissolved in the culture fluid.

INDUSTRIAL APPLICABILITY

The present disclosure can provide a culture bag capable of suppressing the occurrence of foaming when oscillating the culture fluid to perform a culture, and performing a culture with high efficiency, and a culture apparatus including the culture bag.

The invention claimed is:

1. A culture bag comprising a culture space accommodating a culture fluid, wherein:
   the culture space is a loop space to allow the culture fluid to circulate therein;
   the culture bag has an inner surface that comes into contact with the culture fluid to be accommodated therein, the inner surface including, at least in part thereof, a region having a concave-convex structure, the concave-convex structure having a plurality of concave portions and a plurality of convex portions neighboring the respective convex portions;
   the region has a composite structure comprising: the concave-convex structure; and a fine structure formed on a surface of the concave-convex structure;
   each of the convex portions in the concave-convex structure has a rectangular shape extending radially in plan view;
   the convex portions are arranged circumferentially at regular intervals;
   the concave-convex structure has a concave-convex pattern with a height H of 10 mm or less, a width W of 100 mm or less, a pitch P of 100 mm or less, and an aspect ratio H/W of 0.1 or more;
   the fine structure has a fine concave-convex pattern with a height h of 200 nm or more and less than 1 mm, a width w of 5 µm or more and less than 1 mm, a pitch p of 200 nm or more and less than 1 mm, and an aspect ratio h/w of 0.5 or more;
   the fine structure is a grid fine concave-convex structure, which has the fine concave-convex pattern in arbitrary two directions substantially orthogonal to each other; and
   the culture space is a doughnut-like space.

2. The culture bag according to claim 1, wherein the fine concave-convex pattern has the height h of 5 µm or more and 50 µm or less, the width w of 5 µm or more and 40 µm or less, and the pitch p of 10 µm or more and 80 µm or less.

3. A culture apparatus comprising the culture bag according to claim 1.

4. A culture bag comprising a culture space accommodating a culture fluid, wherein:
   the culture space is a loop space to allow the culture fluid to circulate therein;
   the culture bag has an inner surface that comes into contact with the culture fluid to be accommodated therein, the inner surface including, at least in part thereof, a region having a concave-convex structure, the concave-convex structure having a plurality of concave portions and a plurality of convex portions neighboring the respective convex portions;
   the region has a composite structure comprising: the concave-convex structure; and a fine structure formed on a surface of the concave-convex structure;
   each of the convex portions in the concave-convex structure has a rectangular shape extending radially in plan view;
   the convex portions are arranged circumferentially at regular intervals;
   the fine structure has a fine concave-convex pattern with a height h of 200 nm or more and less than 1 mm, a width w of 5 µm or more and less than 1 mm, and a pitch p of 200 nm or more and less than 1 mm; and the fine structure is a grid fine concave-convex structure, which has the fine concave-convex pattern in arbitrary two directions substantially orthogonal to each other.

* * * * *